United States Patent [19]

Lippsmeier et al.

[11] 4,076,755
[45] Feb. 28, 1978

[54] PRODUCTION OF HYDROXYALKYLPHOSPHINE OXIDES

[75] Inventors: Bernd Lippsmeier, Hurth-Knapsack; Klaus Hestermann, Erftstadt-Bliesheim, both of Germany

[73] Assignee: Hoechst Aktiengesellschaft, Frankfurt am Main, Germany

[21] Appl. No.: 666,699

[22] Filed: Mar. 15, 1976

[30] Foreign Application Priority Data

Mar. 19, 1975  Germany .............................. 2511932

[51] Int. Cl.² .............................................. C07F 9/53
[52] U.S. Cl. ............................................ 260/606.5 P
[58] Field of Search ................................ 260/606.5 P

[56]  References Cited
U.S. PATENT DOCUMENTS

| | | | |
|---|---|---|---|
| 3,030,421 | 4/1962 | Reuter et al. | 260/606.5 P |
| 3,636,160 | 1/1972 | Carlson | 260/606.5 P |
| 3,660,495 | 5/1972 | Lin | 260/606.5 P |
| 3,683,028 | 8/1972 | Haas | 260/606.5 P |
| 3,852,362 | 12/1974 | Lambert | 260/606.5 P |

OTHER PUBLICATIONS

Petrov, et al., Russ. Chem. Rev., V37, 532–537, (1968).

*Primary Examiner*—Helen M. S. Sneed
*Attorney, Agent, or Firm*—Connolly and Hutz

[57] ABSTRACT

Production of tertiary hydroxyalkylphosphine oxides of general formula (I)

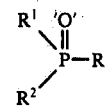

in which $R^1$ and $R^2$ each stand for organic groups having from 1 to 18 carbon atoms, where $R^1$ may be identical with $R^2$ and $R^2$ may be identical with R which stands for a radical of general formula (II)

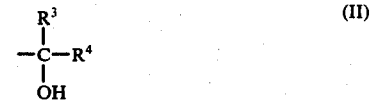

in which $R^3$ and $R^4$ equally stand for organic groups having from 1 to 18 carbon atoms and/or more preferably for hydrogen. The compounds are made from phosphines of general formula (III)

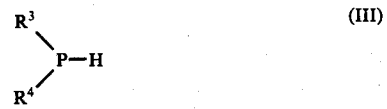

in which $R^3$ and $R^4$ have the meanings given above, which are reacted in a single step operation with carbonyl compounds of general formula (IV)

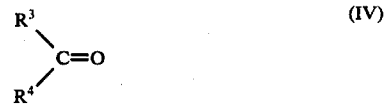

in which $R^3$ and $R^4$ equally have the meanings given above. The reaction is effected while adding at least one substance yielding hydroxyl ions and in the presence of water, and the resulting hydroxyalkylphosphine oxides are separated from the reaction product.

16 Claims, No Drawings

PRODUCTION OF HYDROXYALKYLPHOSPHINE OXIDES

The present invention relates to a process for making tertiary hydroxyalkylphosphine oxides of general formula (I)

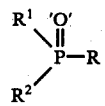
(I)

in which $R^1$ and $R^2$ each stand for branched and/or unbranched, identical and/or different alkyl, cycloalkyl, aryl, alkylaryl and aralkyl groups having from 1 to 18 carbon atoms, preferably from 1 to 6 carbon atoms, more preferably 1 to 2 carbon atoms, where $R^1$ may be identical with $R^2$ and $R^2$ may be identical with R, which stands for a radical of the following general formula (II)

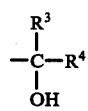
(II)

in which $R^3$ and $R^4$ each stand for branched and/or unbranched, identical and/or different alkyl, cycloalkyl, aryl, alkylaryl and aralkyl groups having from 1 to 18 carbon atoms and/or more preferably for hydrogen atoms.

The process of the present invention is particularly well adapted for making tris-(hydroxymethyl)-phosphine oxide, bis-(hydroxymethyl)-methylphosphine oxide and (hydroxymethyl)-dimethylphosphine oxide.

It has been described that tertiary hydroxyalkylphosphine oxides can be made by a process, wherein hydroxyalkyl phosphines, produced in a separate operation, are treated with one or more oxidants and thereby transformed into the corresponding phosphine oxides (Houben-Weyl, Methoden der org. Chemie, Georg Thieme Verlag, Stuttgart, vol. XII/1, pages 135 et seq. (1963)), and (G. M. Kosolapoff and L. Maier, Organic Phosphorus Compounds, vol. 3, Wiley-Interscience, New York, pages 341 et seq. (1972)).

Compounds, such as tris-(hydroxymethyl)-phosphine oxide, bis-(hydroxymethyl)-methylphosphine oxide or bis-(hydroxymethyl)-phenylphosphine oxide are more particularly obtained by subjecting suitable tertiary phosphines to oxidation by means of aqueous hydrogen peroxide solutions (cf. German Patent Specification No. 1 040 549; E. I. Grinstein, A. B. Bruker and L. Z. Soborowskii, Doklady Akad. USSR 139, 1359 (1961); W. Wegener and P. Scholz, Z. Chem. vol. 12 (1972) (9), 334).

It has also been described that tris-(hydroxymethyl)-phosphine oxide can be made by a two step-process, wherein $PH_3$ is initially reacted with formaldehyde under pressure to give tris-(hydroxymethyl)-phosphine semiacetal and this latter compound is then oxidized and transformed into the semiacetal of tris-(hydroxymethyl)-phosphine oxide. Water and formaldehyde are then stripped off with the resultant formation of tris-(hydroxymethyl)-phosphine oxide (U.S. Patent Specification No. 3 636 160 (1972)).

These prior processes are not fully satisfactory in respect of the following points: They are carried out in at least two steps. In addition to this, it is necessary for the tertiary phosphines to be separated intermediarily and partially under pressure. Still further, these prior processes use oxidants, such as hydrogen peroxide, nitric acid, oxygen, ozone, which are very likely to initiate uncontrollable side reactions, e.g. the formation of peroxide intermediates, that may give rise to explosions, and handicap operation on a commercial scale (Houben-Weyl, Methoden der org. Chemie, Georg Thieme Verlag, Stuttgart, vol. XII/1, pages 140 et seq. (1963)).

In addition to this, the above oxidants often cause P-C-bonds to be partially broken up with the resultant formation of oxidation end products, such as phosphinic acids, phosphonic acids or even phosphates, whereby the production of pure hydroxyalkylphosphine oxides is rendered difficult or even impossible.

In view of this it was all the more an unexpected result that compounds of general formula (I) are readily obtainable in a smooth reaction comprising subjecting phosphines of general formula (III)

(III)

in which $R^3$ and $R^4$ have the meanings given above to a single step-reaction with carbonyl compounds of general formula (IV)

(IV)

in which $R^3$ and $R^4$ equally have the meanings given above, the reaction being effected while adding one or more substances yielding hydroxyl ions and in the presence of water, and separating the resulting hydroxyalkylphosphine oxides from the reaction product obtained.

An even more unexpected result resides in the fact that the carbonyl compounds of formula (IV) are substantially not subject to side-reactions, such as aldol condensation or Cannizarro reaction, in the presence of OH-ions in an aqueous alkaline medium.

It is a further unexpected result that the reaction, which occurs as some sort of a single pot reaction, takes a smooth course with the resultant direct formation, i.e. without any need to isolate phosphine intermediates, of tertiary hydroxyalkylphosphine oxides, which are obtained in high yields.

The substances yielding hydroxyl ions, which may be used in the process of the present invention, preferably comprise water-soluble bases, such as NaOH, KOH or $NH_4OH$ or alkyl ammonium hydroxides, and phosphonium hydroxides corresponding to the particular phosphine of formula (III) and having general formula (V)

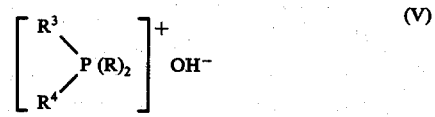
(V)

in which the substituents R, $R^3$ and $R^4$ have the meanings given above. The phosphonium hydroxides comprise, e.g. [P(CH$_2$OH)$_4$]OH, [CH$_3$P(CH$_2$OH)$_3$]OH or [(CH$_3$)$_2$P(CH$_2$OH$_2$]OH.

The catalytically active and hydroxyl ion-yielding substances should preferably be added to the reaction mixture in quantities enabling the latter to be maintained at a pH-value between 8 and 13.5, preferably between 8.5 and 11.5. In other words, it is necessary for the catalyst to be used in proportions of several percent, based on the total mixture.

The reaction temperatures should range from 0° to 120° C, preferably from 25° to 95° C.

With respect to the reaction mixture, it is possible for it to be admixed with water and with a further solvent preferably with an alcohol, such as methanol, ethanol or propanol.

Particularly useful phosphines of formula (III) above are PH$_3$, CH$_3$PH$_2$ and (CH$_3$)$_2$PH.

The reaction should preferably be effected at atmospheric pressure in an agitator-provided reactor or column. It is also preferable for the reaction to be effected under inert gas, e.g. under nitrogen, carbon dioxide or argon.

The hydroxyalkylphosphines oxide made by the process of the present invention are obtained in good yields and are very pure (97 – 99%). Once the aqueous phase, which consists of water or a water/solvent-mixture, has been removed, they are easy to separate from the reaction product in known fashion, e.g. by distillation under vacuum.

In carrying out the process of the present invention, it is good practice to introduce the carbonyl compound into an aqueous phase, which may be water or a water/solvent-mixture. Following this, a pH-value between 8 and 13.5 is established in the aqueous phase by means of a substance yielding hydroxyl ions and the phosphine of formula (III) is added, gaseous phosphine being introduced continuously, and liquid or solid and dissolved phosphine being added dropwise. After the reaction, which takes place at temperatures of from 0° to 120° C, with evolution of hydrogen, is complete, the hydroxyalkylphosphine oxide of formula (I) is separated from the reaction product obtained.

The process of the present invention compares favorably with the prior art methods, primarily in respect of the following points: it is carried out as a one-step process without any need to separate intermediate products. It is carried out under atmospheric pressure, takes a smooth course and produces good yields of very pure and uniform final products which are easy to separate. The only by-product obtained in significant proportions is hydrogen which escapes in gas form.

The compounds made by the process of the present invention partially find use as valuable flameproofing agents and partially as valuable intermediates for making other flameproofing materials, plant protecting agents, and pharmaceutical preparations.

EXAMPLE 1

(The percentages in the following Examples are by weight unless otherwise stated)

222.4 g of a 27% aqueous formaldehyde solution was placed in a reactor provided with an agitator, reflux condenser, thermometer, gas inlet and pH-meter, and a pH-value of 10.0 was established by means of a 5% sodium hydroxide solution, under nitrogen. The resulting solution was throughly agitated at 35° to 40° C and gaseous methylphosphine was rapidly introduced so that it ceased to be absorbed after 3 hours. During the reaction, the pH-value was found to drop down to about 9.1 to 9.3. Altogether 50 g (1.04 mol) of methylphosphine was introduced. During the introduction, hydrogen was found to evolve and to escape in gas form from the reaction mixture. It was burnt in an incinerator system placed downstream of the reactor, for reasons of safety.

The whole was heated for a further 1.5 to 2 hours to 90° – 95° C so as to terminate the reaction. This was recognizable by the fact that hydrogen ceased to be evolved. Following this, the water was removed by distillation under vacuum at temperatures up to 120° C under a pressure of 20 mm Hg. 117.8 g of a clear viscous product, which crystallized on standing, was obtained. It was high-grade (more than 98%) bis-(hydroxymethyl)-methylphosphine oxide which contained traces of formaldehyde and water together with 0.08% of trivalent phosphorus compounds. The product had a melting point of 67° – 69° C. It was obtained in a yield of 91.2%, based on methylphosphine. The product was recrystallized e.g. from dimethylformamide or ethanol and then had a melting point of 70° – 71° C. The recrystallized product was found to be identical in its physical and chemical properties with comparative products made by the processes described by E. I. Grinstein et al., Doklady Akd. USSR, 139, 1359 (1961) and in German Patent Specification "Offenlegungsschrift" 2 319 043, respectively.

| | Analysis: C$_3$H$_9$O$_3$P | | |
|---|---|---|---|
| Calculated: | C 29.0 % | H 7.3 % | P 25.0 % |
| Found: | C 28.8 % | H 7.3 % | P 24.9 % |

It was possible for the yield, based on CH$_3$PH$_2$, to be increased substantially to 100%. To this end, it was necessary for the hydrogen evolved to be treated in a gas scrubbing stage, e.g. a scrubbing column, downstream of the agitator-provided reactor, with an aqueous formalin solution and to be freed thereby from carried-over methylphosphine. The scrubbing solution was recycled to the agitator-provided reactor and used for preparing a new batch therein and reacted in the manner described to give bis-(hydroxymethyl)-methylphosphine oxide.

EXAMPLE 2

NaOH as the substance yielding OH-ions was replaced by a tris-(hydroxymethyl)-methylphosphonium hydroxide-catalyst, and the same result as that described in Example 1 was obtained under the conditions reported therein.

In the present Example, the catalyst was added in the proportions necessary to establish a pH-value of 9.8 – 10.1 (about 1 – 3% based on formalin).

In this case, it is impossible for cations, such as Na-ions to go forward into the reaction product, which is advantageous. 222 g of 27% aqueous formalin solution gave 120.9 g of 98.2% bis-(hydroxymethyl)-methylphosphine oxide.

After having been recrystallized, the product had a melting point of 71° C. The yield was almost quantitative, and the product was identical with that prepared in the manner described in Example 1.

EXAMPLE 3

The procedure was the same as that described in Example 1 save that a formaldehyde solution in a methanol/water-mixture (ratio of methanol to water = 2:1 parts) was used. Bis-(hydroxymethyl)-methylphosphine oxide (purity more than 98%) was obtained again in almost quantitative yield.

EXAMPLE 4

The procedure was the same as that described in Example 1. 222.2 g of a 27% aqueous formalin solution which contained 0.35 g of cadmium chloride (CdCl$_2$ . H$_2$O) was placed in the reactor. Gaseous hydrogen phosphide was introduced at 25° – 30° C with the resultant formation of a minor amount of dissolved tetrakis-(hydroxymethyl)-phosphonium hydroxide. In this manner a pH-value of 10.8 to 10.9 was established. The pH-value was maintained, the temperature was increased up to at most 45° – 50° C and the material was reacted with further PH$_3$ until the reaction was complete. Following this, the whole was heated for a further period of 2 to 3 hours to 75° C and a pH-value of 4.0 to 4.2 was established by adding several drops of dilute hydrochloric acid. The water was removed by distillation under vacuum (60° C; 1–2 mm Hg) and 93 g of a colorless, viscous and hygroscopic residue was obtained. It was allowed to cool and crystallize (melting point: 46° – 48° C).

The reaction product was tris-(hydroxymethyl)-phosphine oxide. It was very pure (more than 97%) and slightly contaminated with minor proportions of catalyst and water or trivalent phosphorus compounds (less than 0.1%).

In its physical and chemical properties (NMR-spectrum, IR-spectrum, solubility) the product so made was identical with, but qualitatively superior to, comparative products made by the process described in German Patent Specification No. 1 040 549 from tris-(hydroxymethyl)-phosphine and hydrogen peroxide, or by the process described in U.S. Patent Specification No. 3 076 034 from tetrakis-(hydroxymethyl)-phosphonium chloride.

The tris-(hydroxymethyl)-phosphine oxide produced in accordance with the present invention (Example 4) is generally ready for use, i.e. awaits no further purifying treatment. In those cases in which it is desirable for the product to be purified further, it is possible for it to be recrystallized from ethanol/benzene or ethanol/isopropanol-mixtures.

The phosphonium base [P(CH$_2$OH)$_4$]OH used in Example 4 may be replaced by NaOH or KOH to establish the necessary pH-range. In this event, however, the resulting tris-(hydroxymethyl)-phosphine oxide is found to contain minor proportions of sodium or potassium ions as further contaminants.

EXAMPLE 5

The procedure was the same as that described in Example 1. 100 g of a 30% aqueous formalin solution was admixed with dilute sodium hydroxide solution (10% strength) so as to establish a pH-value of 11.0 to 11.3. Following this, gaseous dimethylphosphine was rapidly introduced at 35° – 40° C so that it was substantially impossible for dimethylphosphine to be carried along by escaping hydrogen. The reaction was substantially complete once dimethylphosphine ceased to be absorbed, which was indicated by an exponential increase of the dimethylphosphine content in the hydrogen off-gas. The reaction mixture was maintained for a further 1 to 2 hours at 70° C and water was removed by distillation under vacuum after that time. 106.4 g of a pale yellow viscous residue was obtained which solidified on cooling. It contained about 97.8% of (hydroxymethyl)-dimethylphosphine oxide and 0.12% of trivalent phosphorus compounds. The product had a melting point of 70° – 72° C and was very hygroscopic.

It was possible for the crude product to be purified by fractional distillation under vacuum (bp 140° C/0.2 mm Hg), or more preferably by introducing a melt thereof into acetone. The product so purified had a melting point of 76° – 77° C.

The (hydroxymethyl)-dimethylphosphine oxide prepared in Example 5 was found to be identical with a comparative product made by the process described by H. J. Kleiner in Liebigs Ann. Chem. 1974, 751 – 764.

We claim:

1. A process for making tertiary hydroxyalkylphosphine oxides of general formula (I)

in which R$^1$ and R$^2$ are identical or different radicals selected from the group consisting of branched and unbranched alkyl, cycloalkyl, aryl, alkylaryl and aralkyl groups having from 1 to 18 carbon atoms, where R$^1$ may be identical with R$^2$ and R$^2$ may be identical with R, which is a radical of general formula (II)

in which R$^3$ and R$^4$ are identical or different radicals selected from the group consisting of branched and unbranched alkyl, cycloalkyl, aryl, alkylaryl and aralkyl groups having from 1 to 18 carbon atoms and hydrogen, which process comprises subjecting phosphines of general formula (III)

in which R$^3$ and R$^4$ have the meanings given above to a single step reaction with carbonyl compounds of general formula (IV)

in which R$^3$ and R$^4$ have the meanings given above, the reaction being effeted by introducing the phosphine of general formula (III) into an aqueous phase containing the carbonyl compound of formula (IV) and being adjusted to a pH-value of from 8 to 13.5 by adding thereto a water soluble base yielding hydroxyl ions selected from the group consisting of NaOH, KOH, NH$_4$OH and phosphonium hydroxides of general formula (V)

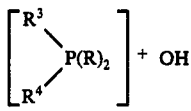

and separating the resulting hydroxyalkylphosphine oxide of general formula (I) from the reaction product obtained.

2. The process as claimed in claim 1, wherein the phosphonium hydroxides of general formula (V) comprise compounds having the following formulae [P(CH$_2$OH)$_4$]OH; [CH$_3$P(CH$_2$OH)$_3$]OH or [(CH$_3$)$_2$P(CH$_2$OH)$_2$]OH.

3. The process as claimed in claim 1, wherein the substance yielding hydroxyl ions is used in the proportions necessary to establish a pH-value of from 8.5 to 11.5.

4. The process as claimed in claim 1, wherein the reaction is effected at temperatures of from 0° to 120° C.

5. The process as claimed in claim 4, wherein the reaction is effected at temperatures of from 25° to 95° C.

6. The process as claimed in claim 1, wherein the reaction mixture is used in admixture with water together with a further solvent.

7. The process as claimed in claim 6, wherein said further solvent is an alcohol.

8. The process as claimed in claim 1, wherein said solvent is methanol, ethanol or propanol.

9. The process as claimed in claim 1, wherein the phosphines of general formula (III) comprise PH$_3$, CH$_3$PH$_2$ or (CH$_3$)$_2$PH.

10. The process as claimed in claim 1, wherein the reaction is carried out at atmospheric pressure.

11. The process as claimed in claim 1, wherein reaction is effected in an agitator-provided reactor or column.

12. The process as claimed in claim 1, wherein the reaction is carried out under inert gas.

13. The process as claimed in claim 12, wherein the reaction is carried out under nitrogen, carbon dioxide or argon.

14. The process as claimed in claim 1, wherein the aqueous phase is removed by distillation under vacuum and the hydroxyalkylphosphine oxides are then separated from the reaction product.

15. The process as claimed in claim 1, which comprises introducing the carbonyl compound of formula (IV) into an aqueous phase, adding the hydroxyl ion-yielding substance so as to establish a pH-value of from 8 to 13.5, introducing the phosphine of general formula (III), effecting the reaction at temperatures of from 0° to 120° C, and separating the resulting hydroxyalkyl-phosphine oxide of general formula (I) from the reaction product obtained.

16. The process as claimed in claim 1 wherein R$_3$ and R$_4$ each are hydrogen.

* * * * *